(12) United States Patent
Siddique et al.

(10) Patent No.: US 12,153,046 B2
(45) Date of Patent: Nov. 26, 2024

(54) ALUMINUM METASURFACES FOR HIGHLY SENSITIVE AND ENHANCED DETECTION OF ANALYTES FOR SMARTPHONE DIAGNOSTICS AND METHODS FOR MAKING AND USING THE SAME

(71) Applicant: Samsung Electronics Co., Ltd., Suwon-si (KR)

(72) Inventors: Radwanul Hasan Siddique, Pasadena, CA (US); Hyuck Choo, Yongin-Si (KR)

(73) Assignee: SAMSUNG ELECTRONICS CO., LTD. (KR)

( * ) Notice: Subject to any disclaimer, the term of this patent is extended or adjusted under 35 U.S.C. 154(b) by 1091 days.

(21) Appl. No.: 17/000,268

(22) Filed: Aug. 21, 2020

(65) Prior Publication Data

US 2021/0223241 A1  Jul. 22, 2021

Related U.S. Application Data (60) Provisional application No. 63/013,524, filed on Apr. 21, 2020, provisional application No. 62/962,923, filed on Jan. 17, 2020.

(51) Int. Cl.
*G01N 33/553* (2006.01)
*B05D 1/00* (2006.01)
(Continued)

(52) U.S. Cl.
CPC ......... *G01N 33/553* (2013.01); *B05D 1/005* (2013.01); *G01N 21/6428* (2013.01);
(Continued)

(58) Field of Classification Search
None
See application file for complete search history.

(56) References Cited

U.S. PATENT DOCUMENTS 9,568,619 B2    2/2017  Hong et al.
2012/0050732 A1  3/2012  Lu et al.
(Continued)

FOREIGN PATENT DOCUMENTS

EP    0389274 A2   9/1990
EP    3279643 A1   2/2018
(Continued)

OTHER PUBLICATIONS

Baldini, F. et al. Optical PMMA Chip Suitable for Multianalyte Detection, IEEE Sensors Journal, vol. 8, No. 7, Jul. 2008, 1305-1309. (Year: 2008).*

(Continued)

*Primary Examiner* — Xiaoyun R Xu
(74) *Attorney, Agent, or Firm* — Renaissance IP Law Group LLP (57) ABSTRACT

A metasurface device includes a dielectric layer, an aluminum nanodisk and an aluminum layer. The dielectric layer includes top and bottom surfaces that are opposite each other. The dielectric layer also includes at least one ring-like cavity that extends between the top and bottom surfaces of the dielectric layer. The aluminum nanodisk is formed in the at least one ring-like cavity in the dielectric layer. The aluminum layer is formed on the dielectric layer and includes at least one ring-like cavity that extends between top and bottom surfaces of the aluminum layer. Each ring-like cavity in the aluminum layer corresponds to a ring-like cavity in the dielectric layer. Two or more analytes may emit fluorescence in response to light of a predetermined wavelength being incident on the metasurface device and in which the two or more analytes are present at the dielectric layer.

8 Claims, 7 Drawing Sheets

(51) Int. Cl.
   *G01N 21/64*   (2006.01)
   *G01N 33/543*  (2006.01)
   *G06F 1/16*    (2006.01)

(52) U.S. Cl.
   CPC ..... *G01N 21/648* (2013.01); *G01N 33/54393* (2013.01); *G01N 2333/515* (2013.01); *G01N 2333/62* (2013.01); *G01N 2333/974* (2013.01); *G06F 1/1684* (2013.01); *H04M 2250/12* (2013.01)

(56) References Cited

U.S. PATENT DOCUMENTS

| | | |
|---|---|---|
| 2016/0187256 A1 | 6/2016 | Bartoli et al. |
| 2017/0090221 A1 | 3/2017 | Atwater |
| 2017/0322418 A1 | 11/2017 | Lin et al. |
| 2018/0156949 A1 | 6/2018 | Tsai et al. |
| 2019/0257986 A1 | 8/2019 | Dominguez et al. |
| 2020/0025610 A1 | 1/2020 | Chandrasekar et al. |
| 2020/0025975 A1 | 1/2020 | Kamali et al. |

FOREIGN PATENT DOCUMENTS

| | | |
|---|---|---|
| WO | 2013154770 A1 | 10/2013 |
| WO | 2019126656 A2 | 6/2019 |

OTHER PUBLICATIONS

Artar, Alp, et al., "Fabry-Pérot nanocavities in multilayered plasmonic crystals for enhanced biosensing," Applied Physics Letters 95, No. 5 (2009), 051105, 3 pages.

Schmidt, Thomas M., et al., "Plasmonic Fluorescence Enhancement of DBMBF 2 Monomers and DBMBF 2—Toluene Exciplexes using Al—Hole Arrays," The Journal of Physical Chemistry, C 118, No. 4 (2014), pp. 2138-2145.

Tramarin, Luca, et al., "Design of an Aluminum/Polymer Plasmonic 2D Crystal for Label-Free Optical Biosensing," Sensors 18, No. 10 (2018), 3335, 12 pages.

Siddique, Radwanul Hasan et al., "Aluminum Metasurface With Hybrid Multipolar Plasmons for 1000-Fold Broadband Visible Fluorescence Enhancement and Multiplexed Biosensing", ACS Nano, Nov. 5, 2019, 25 pages.

Siddique, Radwanul Hasan et al., "Aluminum Metasurface With Hybrid Multipolar Plasmons for 1000-Fold Broadband Visible Fluorescence Enhancement and Multiplexed Biosensing", Supplementary Information, ACS Nano, Nov. 5, 2019, 12 pages.

Huang, Cheng et al., "Polymer Blend Lithography for Metal Films: Large-Area Patterning with Over 1 Billion Holes/Inch2," Beilstein Journal of Nanotechnology, 2015, 6, May 2015, pp. 1205-1211.

* cited by examiner

ALUMINUM METASURFACES FOR HIGHLY SENSITIVE AND ENHANCED DETECTION OF ANALYTES FOR SMARTPHONE DIAGNOSTICS AND METHODS FOR MAKING AND USING THE SAME

CROSS-REFERENCE TO RELATED APPLICATIONS

This application claims the priority benefit under 35 U.S.C. § 119(e) of U.S. Provisional Application No. 62/962,923, filed on Jan. 17, 2020, and to Provisional Application No. 63/013,524, filed on Apr. 21, 2020, the disclosures of which are incorporated herein by reference in their entirety.

TECHNICAL FIELD

The subject matter disclosed herein relates to biosensors. More specifically, the subject matter disclosed herein relates to an aluminum metasurface for use in a biosensor and a method for making the aluminum metasurface.

BACKGROUND

Traditional immunoassay platforms are bulky, expensive, time-consuming, require big tools and equipment, and provide low sensitivity. Most metal-based immunoassay platforms include nanoparticles and are expensive and time-consuming for a detectable reaction. Although metal-based immunoassay platforms may provide a higher level of sensitivity, they may include gold (Au) or silver (Ag), which is expensive. Aluminum (Al) may be used as an alternative to gold and silver, however, aluminum is lossy in the visible spectrum and to date has not been a good plasmonic material that provides analyte detection enhancement. Moreover, bioanalytes do not stick well to metals, so it may be difficult to capture target molecules on a metal surface. Using an adhesive coating on a metal to improve adhesion of bioanalytes to metal may reduce detection enhancement.

SUMMARY

An example embodiment provides a metasurface device that may include a substrate, a dielectric layer, an aluminum nanodisk, and an aluminum layer. The dielectric layer may be formed on the substrate and may include a first surface and a second surface that is opposite the first surface and that interfaces with a surface of the substrate. The dielectric layer may include at least one ring-like cavity that extends between the first surface and the second surface of the dielectric layer. The aluminum nanodisk may be formed in the at least one ring-like cavity in the dielectric layer. The aluminum nanodisk may include a first surface and a second surface that is opposite the first surface and that interfaces with the surface of the substrate. The aluminum layer may be formed on the dielectric layer and may include a first surface and a second surface that is opposite the first surface and that interfaces with the first surface of the dielectric layer. The aluminum layer may include at least one ring-like cavity that extends between the first surface and the second surface of the aluminum layer. Each ring-like cavity in the aluminum layer may correspond to a ring-like cavity in the dielectric layer. In one embodiment, the dielectric layer may include polymethyl methacrylate (PMMA). In another embodiment, two or more analytes emit fluorescence in response to light of a predetermined wavelength being incident on the metasurface device and the two or more analytes being present at the dielectric layer. In still another embodiment, the two or more analytes emit fluorescence in a resonant mode of the metasurface device that is higher than a dipolar mode of the metasurface device.

An example embodiment provides a metasurface immunoassay biosensor that may include a substrate, a dielectric layer, an aluminum nanodisk and an aluminum layer. The dielectric layer may be formed on the substrate. The dielectric layer may include a first surface and a second surface that is opposite the first surface and that contacts a surface of the substrate. The dielectric layer may include at least one aperture that extends between the first surface and the second surface of the dielectric layer. The aluminum nanodisk may be formed in the at least one aperture in the dielectric layer and may include a first surface and a second surface that is opposite the first surface and that contacts the surface of the substrate. The aluminum layer may be formed on the dielectric layer. The aluminum layer may include a first surface and a second surface that is opposite the first surface and that contacts the first surface of the dielectric layer. The aluminum layer may include at least one aperture that extends between the first surface and the second surface of the aluminum layer. Each aperture in the aluminum layer corresponding to an aperture in the dielectric layer. Two or more analytes may emit fluorescence in response to light of a predetermined wavelength being incident on the metasurface immunoassay biosensor and the two or more analytes being present at the dielectric layer. The two or more analytes may emit fluorescence in a resonant mode of the metasurface immunoassay biosensor that is higher than a dipolar mode of the metasurface immunoassay biosensor. In one embodiment, the two or more analytes may include biomarkers for insulin, vascular endothelial growth factor (VEGF), and thrombin, and a concentration of each of the two or more analytes may be equal to 1 fmol in a single 10 µL droplet. In one embodiment, a distance between the first surface of the aluminum nanodisk and the second surface of the aluminum layer in the at least one aperture in the dielectric layer may be equal to or less than 10 nanometers.

An example embodiment provides a method to make a metasurface device in which the method may include: forming a coating of two phase-separated polymers on a substrate, the phase-separated polymers comprising a first polymer and a second polymer; phase separating polymers of the coating to form at least one droplet in the coating, the first polymer forming the at least one droplet; removing the at least one droplet from the coating to form at least one ring-like cavity in the coating, the ring-like cavity extending from a first surface of the coating to a second surface of the coating that is opposite the first surface of the coating and that contacts the substrate; and forming a layer of aluminum on the coating remaining after the at least one droplet has been removed, the layer of aluminum forming a nanodisk in the at least one ring-like cavity. In one embodiment, the layer of aluminum on the coating that remains after the at least one droplet has been removed may include a first surface and a second surface that is opposite the first surface in which the second surface contacts the first surface of the coating, the first polymer may include polystyrene (PS) and the second polymer may include polymethyl methacrylate (PMMA), the nanodisk may include a first surface and a second surface that is opposite the first surface and that is proximate to the substrate, and a distance between the first surface of the nanodisk and the second surface of the layer of aluminum may be equal to or less than 10 nanometers.

BRIEF DESCRIPTION OF THE DRAWING

In the following section, the aspects of the subject matter disclosed herein will be described with reference to exemplary embodiments illustrated in the figure, in which.

DETAILED DESCRIPTION

In the following detailed description, numerous specific details are set forth in order to provide a thorough understanding of the disclosure. It will be understood, however, by those skilled in the art that the disclosed aspects may be practiced without these specific details. In other instances, well-known methods, procedures, components and circuits have not been described in detail not to obscure the subject matter disclosed herein.

Reference throughout this specification to "one embodiment" or "an embodiment" means that a particular feature, structure, or characteristic described in connection with the embodiment may be included in at least one embodiment disclosed herein. Thus, the appearances of the phrases "in one embodiment" or "in an embodiment" or "according to one embodiment" (or other phrases having similar import) in various places throughout this specification may not be necessarily all referring to the same embodiment. Furthermore, the particular features, structures or characteristics may be combined in any suitable manner in one or more embodiments. In this regard, as used herein, the word "exemplary" means "serving as an example, instance, or illustration." Any embodiment described herein as "exemplary" is not to be construed as necessarily preferred or advantageous over other embodiments. Additionally, the particular features, structures, or characteristics may be combined in any suitable manner in one or more embodiments. Also, depending on the context of discussion herein, a singular term may include the corresponding plural forms and a plural term may include the corresponding singular form. Similarly, a hyphenated term (e.g., "two-dimensional," "pre-determined," "pixel-specific," etc.) may be occasionally interchangeably used with a corresponding non-hyphenated version (e.g., "two dimensional," "predetermined," "pixel specific," etc.), and a capitalized entry (e.g., "Counter Clock," "Row Select," "PIXOUT," etc.) may be interchangeably used with a corresponding non-capitalized version (e.g., "counter clock," "row select," "pixout," etc.). Such occasional interchangeable uses shall not be considered inconsistent with each other.

Also, depending on the context of discussion herein, a singular term may include the corresponding plural forms and a plural term may include the corresponding singular form. It is further noted that various figures (including component diagrams) shown and discussed herein are for illustrative purpose only, and are not drawn to scale. Similarly, various waveforms and timing diagrams are shown for illustrative purpose only. For example, the dimensions of some of the elements may be exaggerated relative to other elements for clarity. Further, if considered appropriate, reference numerals have been repeated among the figures to indicate corresponding and/or analogous elements.

The terminology used herein is for the purpose of describing some example embodiments only and is not intended to be limiting of the claimed subject matter. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The terms "first," "second." etc., as used herein, are used as labels for nouns that they precede, and do not imply any type of ordering (e.g., spatial, temporal, logical, etc.) unless explicitly defined as such. Furthermore, the same reference numerals may be used across two or more figures to refer to parts, components, blocks, circuits, units, or modules having the same or similar functionality. Such usage is, however, for simplicity of illustration and ease of discussion only; it does not imply that the construction or architectural details of such components or units are the same across all embodiments or such commonly-referenced parts/modules are the only way to implement some of the example embodiments disclosed herein.

It will be understood that when an element or layer is referred to as being on, "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

The terms "first." "second," etc., as used herein, are used as labels for nouns that they precede, and do not imply any type of ordering (e.g., spatial, temporal, logical, etc.) unless explicitly defined as such. Furthermore, the same reference numerals may be used across two or more figures to refer to parts, components, blocks, circuits, units, or modules having the same or similar functionality. Such usage is, however, for simplicity of illustration and ease of discussion only; it does not imply that the construction or architectural details of such components or units are the same across all embodiments or such commonly-referenced parts/modules are the only way to implement some of the example embodiments disclosed herein.

Unless otherwise defined, all terms (including technical and scientific terms) used herein have the same meaning as commonly understood by one of ordinary skill in the art to which this subject matter belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The subject matter disclosed herein provides an aluminum metasurface for use in a biosensor that may be part of a point of care (POC) device embodied in a handheld device, such as a smartphone. In one embodiment, the aluminum metasurface biosensor disclosed herein may be produced using a low-cost spray and spin-coating technique, and an aluminum thin-film deposition technique. Alternatively, the aluminum metasurface sensor may be produced using a low-cost inkjet printing technique, and an aluminum thin-film deposition technique.

The aluminum metasurface disclosed herein includes nanoantennas formed from aluminum nanoantennas of nanodisks-in-submicron-cavities (nDISCs). The nDISC nanoantennas may generate hybrid multipolar lossless plasmonic modes to significantly enhance local electromagnetic fields and increase the local density of states of the coupled emitter throughout the visible-light spectrum. Thus, the metasurface disclosed herein provides a highly efficient electromagnetic field confinement in visible-light wavelengths by the nanoantennas, which favors real-world plasmonic applications of aluminum over other noble metals. In one embodiment, the aluminum metasurface sensor may utilize low-loss higher-order plasmons to provide a high detection sensitivity with simultaneous electromagnetic and chemical enhancement and improved light emission that may be redirected to a detector with up to a 3-fold enhancement.

In one embodiment, the aluminum metasurface may be used to simultaneously detect multiple biomarkers at low concentrations. For example, three biomarkers (insulin, vascular endothelial growth factor, and thrombin relevant to diabetes, ocular and cardiovascular diseases) may be simultaneously detected in a single 10-μL droplet containing only 1 fmol of each biomarker using the metasurface disclosed herein and a multiplexing technique involving three visible wavelengths.

Near-field enhancement of optical signals from biomolecules via optical nanoantenna has played a significant role in breakthroughs in areas, such as single molecule fluorescence-driven DNA sequencing, sensitive biosensing for early disease detection, and analyzing biochemical interactions. While noble metals like gold and silver have been the dominant materials of choice for such applications, search for alternative options that are more cost-effective and robust has led to detailed exploration of other materials, such as aluminum and titanium nitride in recent years. Aluminum may have the potential to become an excellent alternative due to its relative abundance, sustainability, and simple processing requirements. Aluminum also has more plasma frequencies that occur at higher energies in comparison to the noble metals. Despite potential promises, aluminum nanoantennas have, nevertheless, mostly been limited to biosensing applications in the ultraviolet (UV) to blue wavelength techniques due to the inherently low quality factors (Q factors) of dipolar surface plasmons resonances (Q: ~2) in the visible range as compared to silver (Q: 5-10) and gold (Q: 10-20 in red). Thus, the weak plasmonic performance of aluminum-based nanoantennas in the visible-light spectrum may necessitate use of more expensive noble metal substrates for rapidly expanding biosensing opportunities.

The aluminum metasurface disclosed herein, however, overcomes the issue of low Q factor by utilizing higher-order plasmonic modes of large aluminum nanoantennas with lower radiative and interband-damping over the optical spectra. Higher-order plasmons may be dark (sub-radiant) in nature with almost zero net-dipole moment, which means that they do not easily couple with incident photons, and are, therefore, are not preferred in optical applications. Very recently, however, it has been shown that the plasmonic dark modes can be bright (super-radiant) and radiative in the far-field of tightly-spaced nanostructures caused by the symmetry-breaking, thereby allowing strong light-matter coupling at a single molecule level to be observed. By employing this principle, the higher-order hybrid plasmon resonance modes of the submicron aluminum nanoantennas may enhance local optical fields and fluorescence emission significantly, resulting in a thousand-fold enhancement in the visible range.

Figure 1:
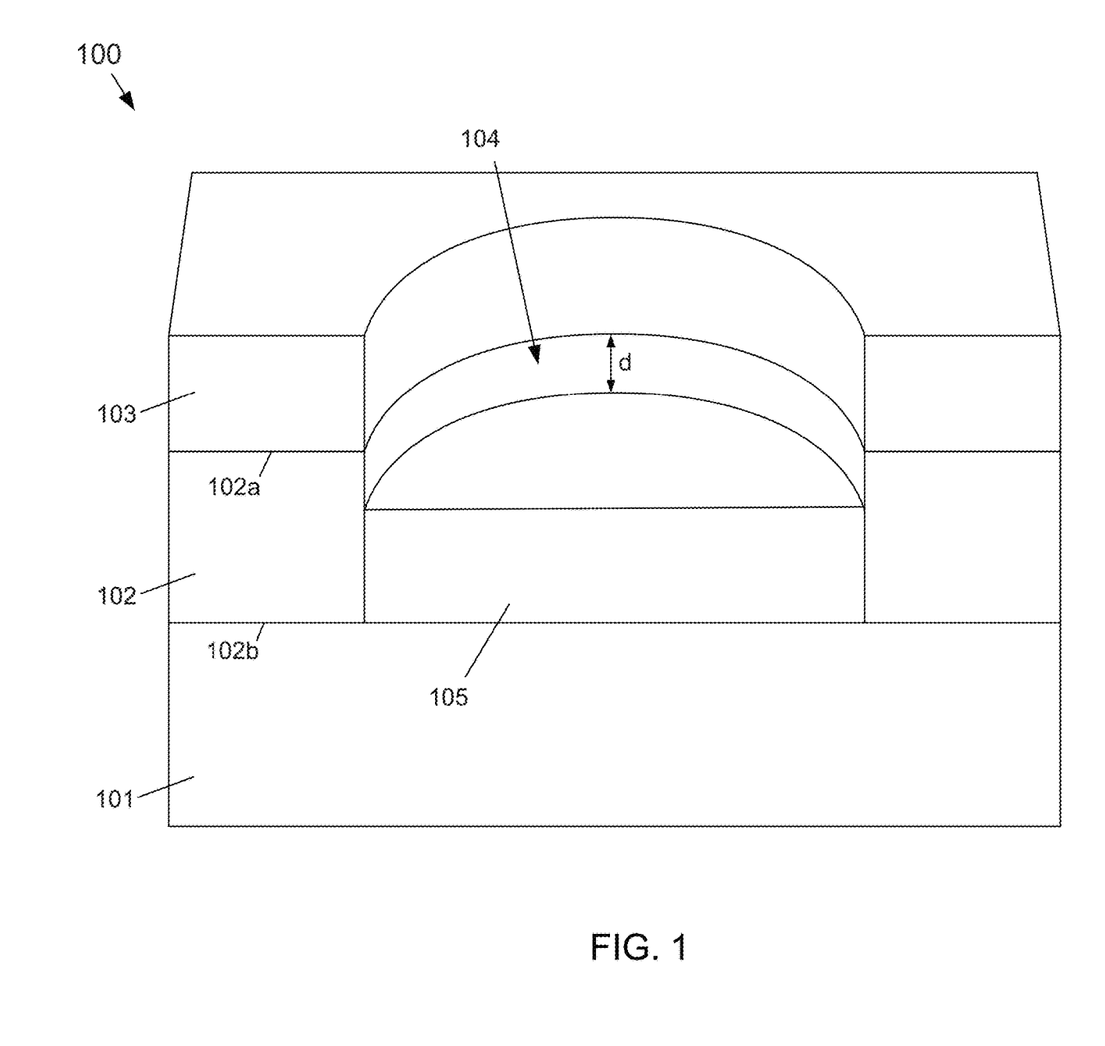
FIG. 1 depicts a perspective cross-sectional view of an example embodiment of an aluminum nDISC according to the subject matter disclosed herein.

FIG. 1 depicts a perspective cross-sectional view of an example embodiment of an aluminum nDISC 100 according to the subject matter disclosed herein. The nDISC 100 nanoantenna may be formed into an array of out-of-plane metal-insulator-metal (MIM) nanoantennas that allows extremely efficient light transfer between the far- and near-fields in the visible-light spectrum. The nDISC nanoantenna 100 may include a substrate 101, a dielectric layer 102 and a metal (aluminum) layer 103. During fabrication, a ring-like cavity, or aperture, 104 is formed in the dielectric layer 102 to extend from a top surface 102a to a bottom surface 102b of the dielectric layer 102. The aluminum layer 103 is deposited on the dielectric layer 102 and an aluminum nanodisk 105 is formed in the cavity 104 on the substrate 101.

In one embodiment, the dielectric layer 103 may be formed from a polymethyl methacrylate (PMMA) polymer. In another embodiment, the dielectric layer 103 may be formed from silicon dioxide ($SiO_2$), however, better results may be obtained using PMMA. In yet other embodiments, other combinations of plasmonic materials and metals may be used. For example, metals and high electrical conductivity materials may be used such as gold, silver, copper, titanium nitride, heavily doped semiconductor layers. Additionally, conductive metal oxides may be used, such as indium-tin-oxide (ITO), aluminum-zinc-oxide (AZO) and gallium-zinc-oxide (GZO).

In one embodiment, a thickness of the nanodisk 105 (and aluminum layer 103) is selected so that a distance d between the bottom surface of aluminum layer 103 and a top surface of the nanodisk 105 is equal to or less than 10 nm. In another embodiment, the distance d is equal to or less than 5 nm. The distance d between the bottom surface of the aluminum layer 103 and a top surface of the nanodisk 105 may provide an optical field confinement that forms what is referred to herein as a hotspot and that allows biomolecules to directly access the hotspots. That is, the sub 10 nm gap of PMMA between the aluminum layer 103 and the aluminum nanodisk 105 may form an electromagnetic hotspot that provides hybrid multipolar plasmonic modes in the visible spectrum that extremely efficiently transfers light between the far- and near-fields visible light fields. Moreover, the PMMA polymer that may be used for the dielectric layer 102 may maximize light transfer, which may allow spatially preconcentrating local molecules at the electromagnetic hotspots spontaneously and further increase a fluorescence signal.

A fluorescence enhancement provided by an aluminum nDISC antenna 100 may occur due to simultaneous boost of local electric field (E) and local density of states (LDOS) on the excitation and emission, respectively, of the emitting molecule due to substantial energy transfer from antenna plasmon modes at the hotspot. Therefore, the maximum theoretical fluorescence enhancement $f_E$ may be calculated by considering field-aligned dipole moments of the emitter:

$$f_E = \left|\frac{E}{E_0}\right|^2 \times \frac{\eta}{\eta_0} \qquad (1)$$

in which E is the enhanced excitation field over the incident electric field $E_0$, $\eta_0$ is the intrinsic quantum efficiency, and $\eta$ account for a modified quantum yield of the fluorescence emitter based on an increase in LDOS.

Figure 2A:
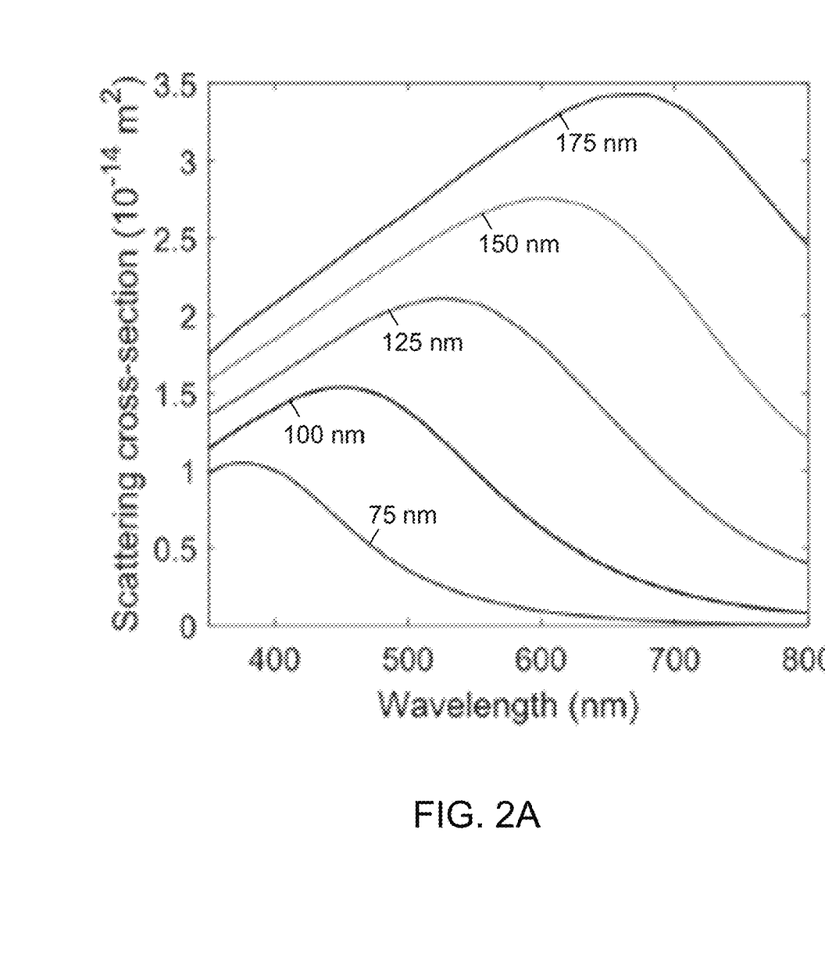
FIG. 2A is a simulated scattering profile of a 75-175 nm lone aluminum nanodisk showing the dipolar resonances peaking in the visible-light spectrum.

A scattering strength of higher-order resonances exhibited by individual (lone) aluminum nanodisk (i.e., nanodisk 105 in FIG. 1) may be extremely poor due to high, non-radiative damping and weak coupling to incident light. Additionally, the dipolar plasmon resonant wavelength and the respective resonance linewidth supported by a lone aluminum nanodisk may rapidly increase as a function of its diameter due to higher radiative damping. For example, FIG. 2A is a simulated scattering profile of a 75-175 nm lone aluminum nanodisk showing the dipolar resonances peaking in the visible-light spectrum. The average Q was found to be only 2.

Figure 2B:
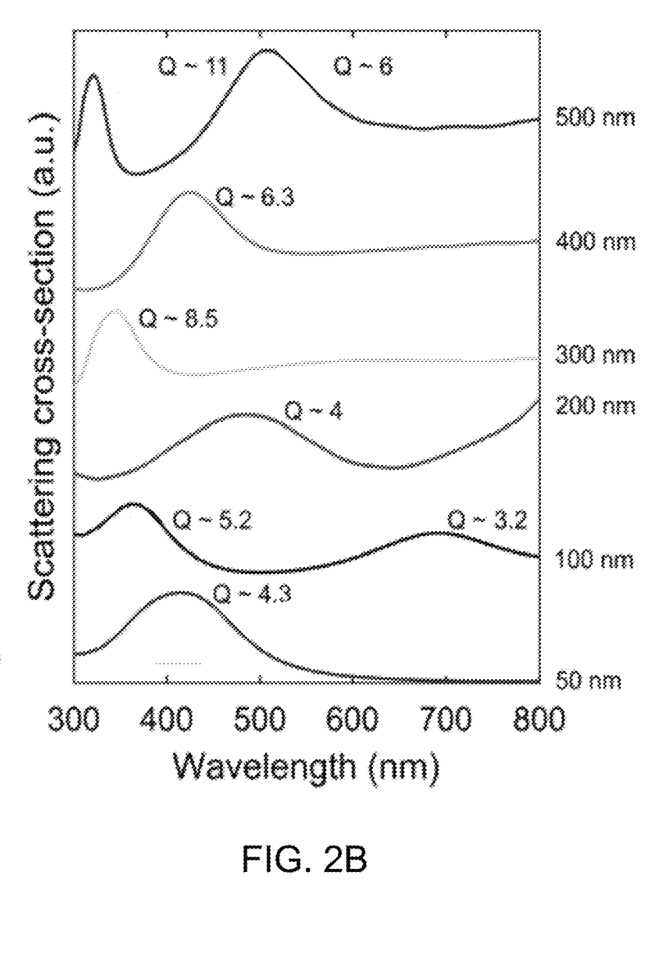
FIG. 2B is a simulated scattering and electric field profiles of nDISC nanoantennas having diameters of 50 nm-500 nm.

In contrast to a lone aluminum nanodisk, FIG. 2B is a simulated scattering and electric field profiles of nDISC nanoantennas having diameters of 50 nm-500 nm. The different diameters for the nDISC nanoantennas are indicated along the ordinate on the right side of FIG. 2B. As shown in FIG. 2B, an nDISC nanoantenna provides strong scattering peaks based on plasmonic hybrid modes. The Q factors of the hybrid modes vary from 4 to 6 in the visible-light spectrum and increase to a Q factor of 11 in UV wavelengths. The radiative damping of the scattering modes decreases especially in higher-order modes which may give rise to a higher quality factor for a larger nDISC nanoantenna. A significant amount of energy may be exchanged between a fluorescent molecule and hybrid multipolar plasmons, thereby resulting in a superior antenna performance in the visible light range for an nDISC nanoantenna.

Radiative components typically determine the overall emission enhancement, whereas photons that couple to non-radiative states undergo interband transitions and do not contribute to the emission process. To single out the effects of radiative $\gamma_r$ and non-radiative $\gamma_{nr}$ components, the contribution from the individual radiative and non-radiative components of an nDISC nanoantenna are plotted in FIG. 3 and compared with a lone aluminum nanodisk antenna. The radiative $\gamma_r/\gamma_0$ and non-radiative $\gamma_{nr}/\gamma_0$ components of an nDISC nanoantenna are respectively indicated by curves 301 and 302 in which $\gamma_0$ is the decay rate of the emitter without the antenna structure/biosensor. For comparison, the radiative $\gamma_r/\gamma_0$ and non-radiative $\gamma_{nr}/\gamma_0$ components of a lone aluminum nanodisk antenna are respectively indicated by curves 303 and 304.

Figure 3:
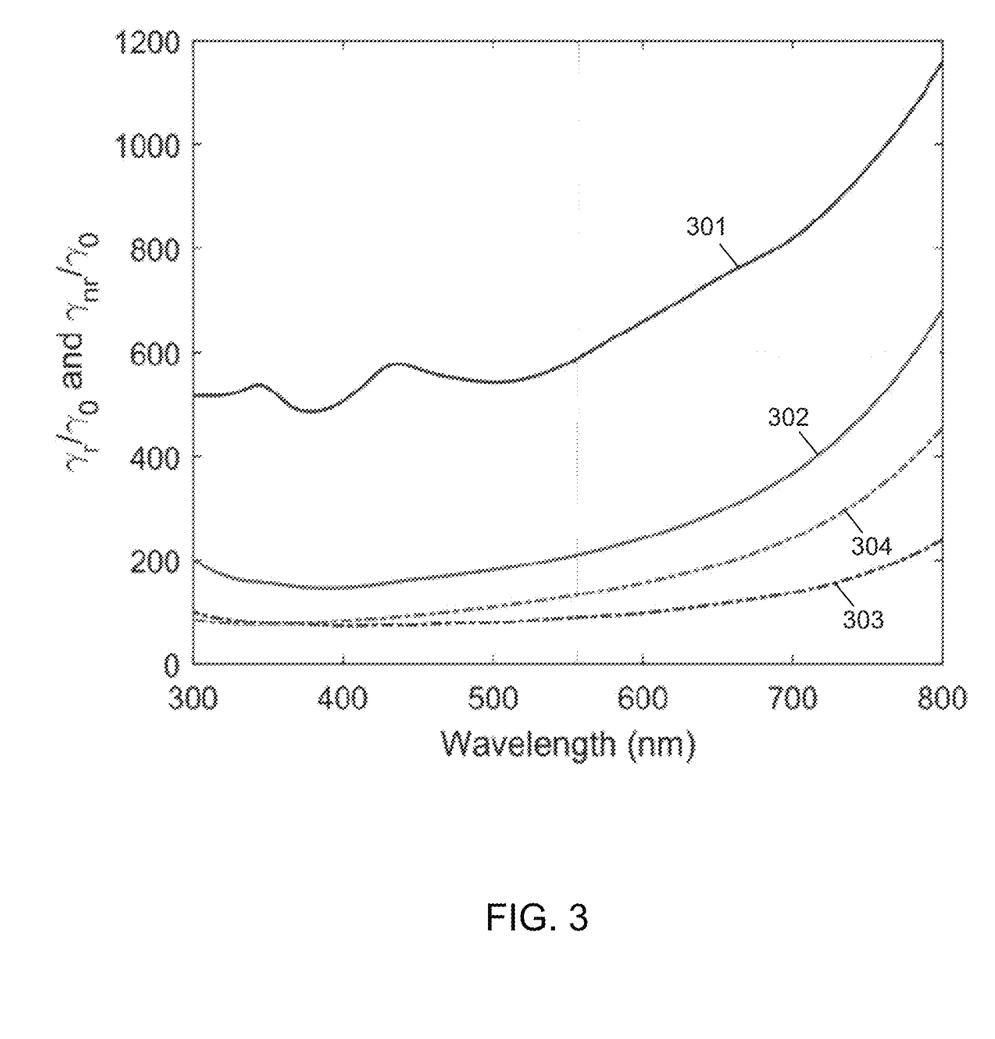
FIG. 3 is a graph showing the contribution from the individual radiative and non-radiative components of an nDISC nanoantenna in comparison to a lone aluminum nanodisk antenna.

The radiative enhancements of an nDISC nanodisk may be dominant in the visible-light spectrum whereas a lone aluminum nanodisk antenna may undergo a large non-radiative enhancement that limits the antenna performance in the same spectral range. Quantitively, radiative (curves 301 and 303) and non-radiative (curves 302 and 304) power components of an emitter respectively experience on average a 6.5 and a 1.8 times increase if the optical antenna design is changed from a lone nanodisk antenna to an nDISC nanoantenna. Notably, an nDISC antenna offers a higher radiative enhancement in comparison to non-radiative enhancement, supporting a positive role played by the strong radiative properties of the higher order modes on emission enhancement.

One example embodiment of a biosensor that may be formed from an array of nDISCs 100 may be used to simultaneously detect multiple biomarkers at low concentrations. Such an example biosensor may be used for early on-chip disease diagnosis or more general multiplexed broadband biosensing that may be provided in a POC device, such as a smartphone or other handheld device, and/or in larger equipment in a clinic. Three different biomarkers for diabetes, ocular and cardiovascular diseases-insulin, vascular endothelial growth factor (VEGF), and thrombin—may be simultaneously sensed by a biosensor formed from an array of nDISCs 100 using a multiplexing technique involving three visible wavelengths. Each of the biomarkers were simultaneously added on nDISC metasurfaces in the form of a 10 μL droplet having a molecular concentration 100 pM, i.e., containing 1 fmol of each biomarker, followed by one hour on-chip incubation. At these very low concentrations, the mean fluorescence signals from the nDISC samples were still significantly higher (about 6- to 10-fold increase in signal intensity) than exhibited by control substrates.

Figure 4A:
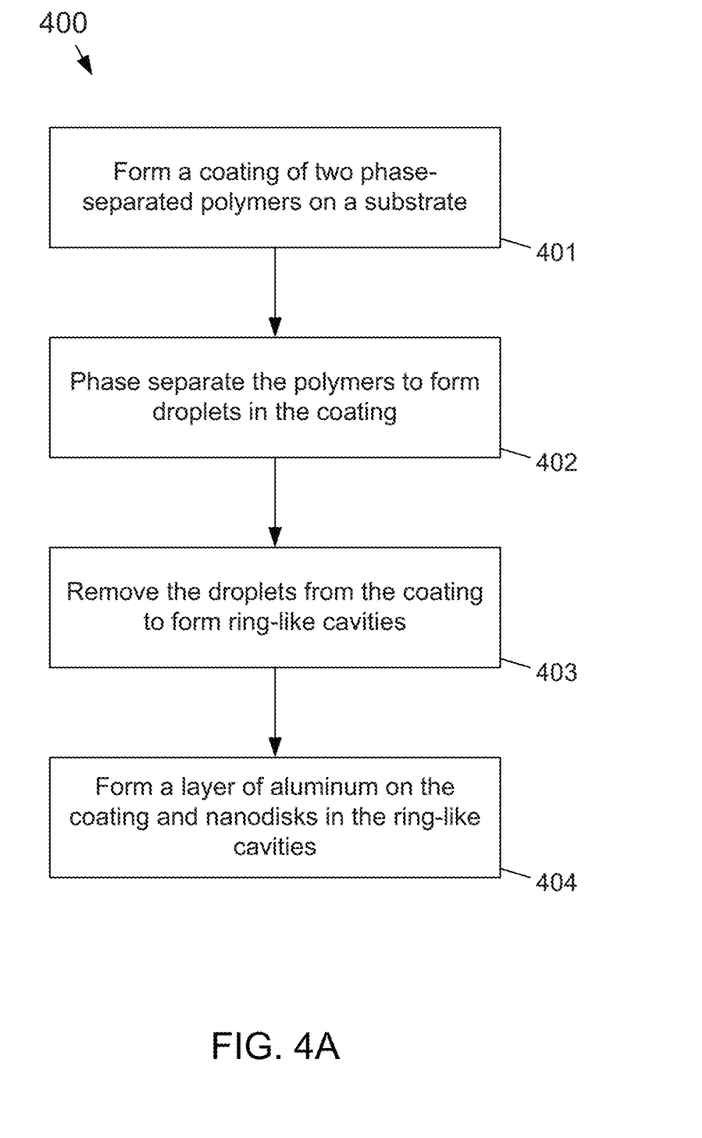
FIG. 4A is a flow diagram of an example embodiment of a process for fabricating an array of nDISC nanoantennas according to the subject matter disclosed herein.
Figure 4B:
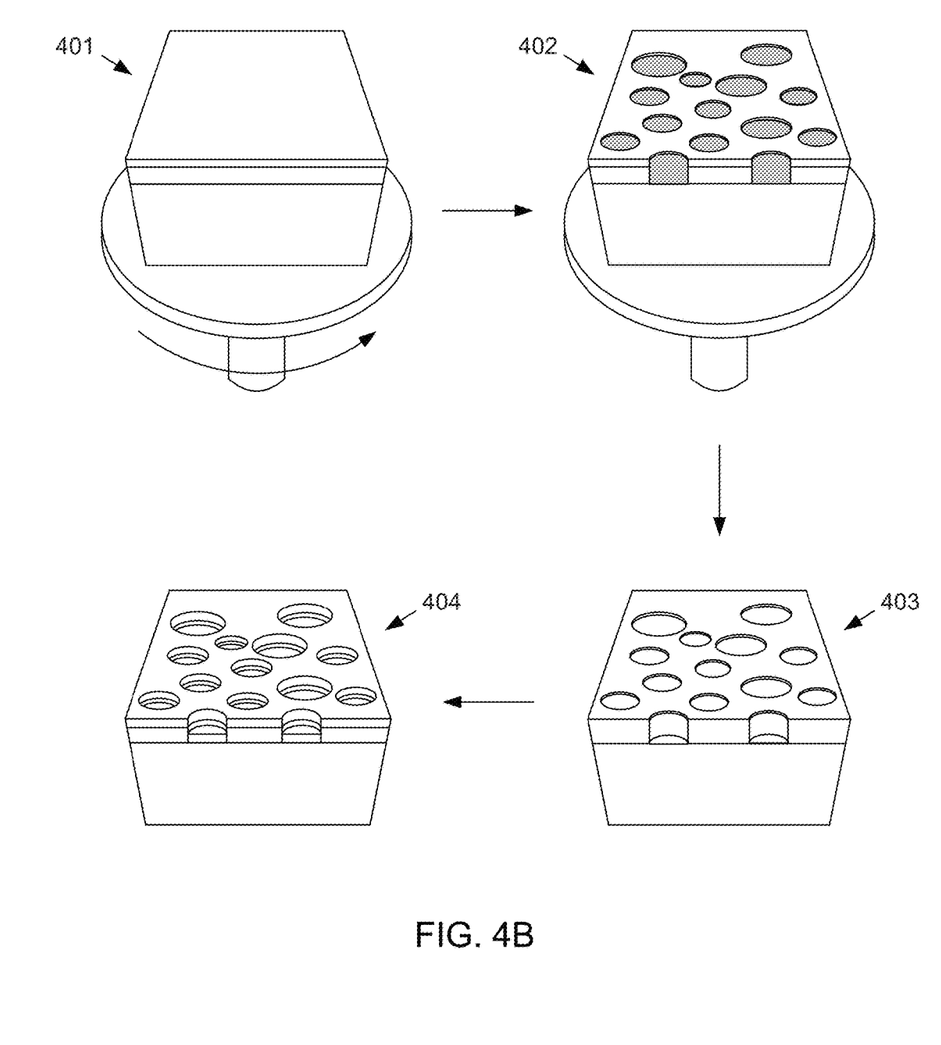
FIG. 4B visually depicts the example embodiment of the process shown in FIG. 4A.

FIG. 4A is a flow diagram of an example embodiment of a process 400 for fabricating an array of nDISC nanoantennas according to the subject matter disclosed herein. FIG. 4B visually depicts the example embodiment of the process 400 in FIG. 4A. Referring to both FIGS. 4A and 4B, at 401 in FIG. 4A a binary polymer-blend solution 411 of two phase-separated polymers is spincoated onto a substrate 412, such as a silicon on insulator (SOI). In one embodiment, the substrate 412 may be flexible or non-flexible. In one embodiment, the binary polymer-blend solution may be PMMA and polystyrene (PS) in a blend solution of butanone. Other possible binary polymer-blend solutions may be formed from two or more immiscible homo-polymers or block copolymers. At 402, the binary polymer-blend solution phase separates forming one or more droplets 413 of one of the two polymers of the solution. At 403, the droplets of the polymer are removed to form ring-like cavities 414. In one embodiment, a diameter of the at least one ring-like cavity 414 may be equal to or less than 0.5 μm. In an alternative embodiment, a dielectric material may be formed on a substrate and the ring-like cavities may be milled using a focused ion beam.

At 404, a layer of aluminum 415 is formed in a well-known manner to cover the remaining polymer-blend solution. Aluminum disks 416 are also formed inside each ring-like cavity 414. In one embodiment, a distance d (FIG. 1) between the top surface of a nanodisk 416 and the bottom surface of the layer of aluminum 415 may be selected to be equal to or less than 10 nm. In another embodiment, the distance d between the top surface of the nanodisk 416 and the bottom surface of the layer of aluminum 215 in the at least one ring-like cavity 414 is equal to or less than 5 nm.

Figure 4C:
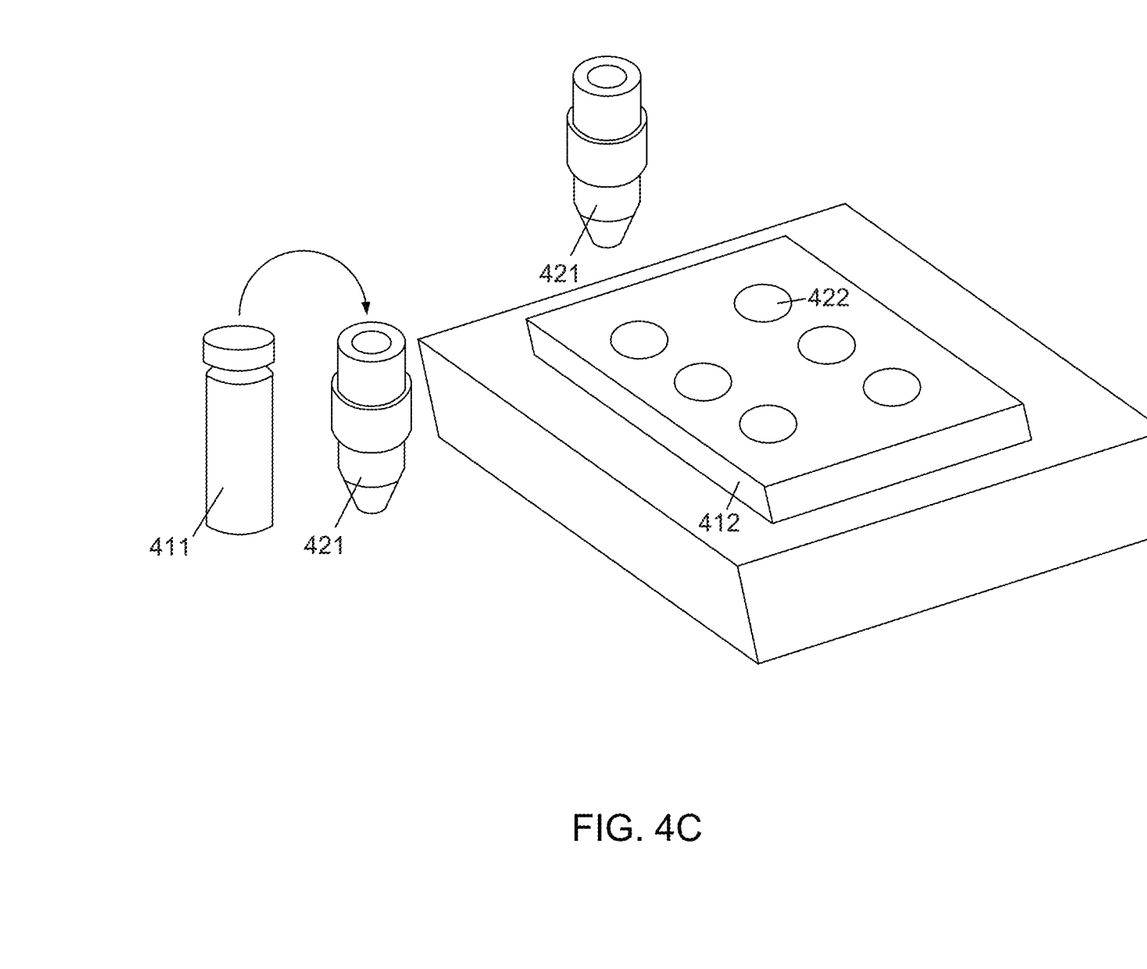
FIG. 4C depicts an example inkjet printing technique in which a binary polymer-blend solution of two phase-separated polymers may be added to a tank of an inkjet printer nozzle according to the subject matter disclosed herein.

In an alternative embodiment for fabricating an array of nDISC nanoantennas, the binary polymer-blend solution 411 may be applied to the substrate 412 using an inkjet printing technique. FIG. 4C depicts an example inkjet printing technique in which the binary polymer-blend solution 411 of two phase-separated polymers may be added to a tank (not shown) of an inkjet printer nozzle 421 according to the subject matter disclosed herein. The binary polymer blend solution 411 is applied to a substrate 412 in a well-known manner to form, for example, biosensors 422. Phase separating and removing droplets of one polymer from the other polymer and forming the aluminum layer and aluminum nanodisks are as described in connection with FIGS. 4A and 4B.

Figure 5:
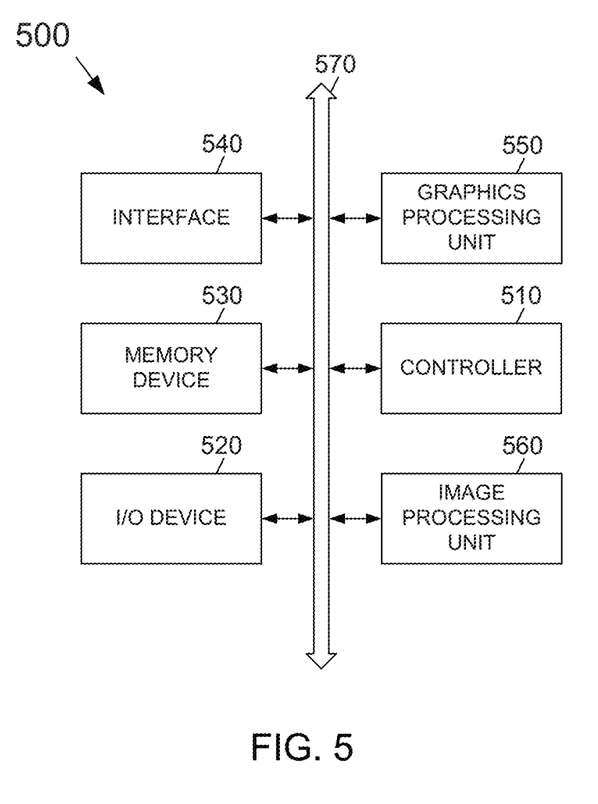
FIG. 5 depicts an electronic device that includes a metasurface for, for example, a POC device according to the subject matter disclosed herein.

FIG. 5 depicts an electronic device 500 that includes a metasurface for, for example, a POC device according to the subject matter disclosed herein. Electronic device 500 may be used in, but not limited to, a computing device, a personal digital assistant (PDA), a laptop computer, a mobile computer, a web tablet, a wireless phone, a cell phone, a smart phone, a digital music player, or a wireline or wireless electronic device. The electronic device 500 may also be part of, but not limited to, an ADAS, a mobile-device imaging system, an industrial imaging system, robotics, etc. The electronic device 500 may include a controller 510, an input/output device 520 such as, but not limited to, a keypad, a keyboard, a display, a touch-screen display, a camera, and/or an image sensor, a memory 530, an interface 540, a GPU 550, and an imaging processing unit 560 that are coupled to each other through a bus 570. The controller 510 may include, for example, at least one microprocessor, at least one digital signal processor, at least one microcontroller, or the like. The memory 530 may be configured to store a command code to be used by the controller 510 or a user data.

Electronic device 500 and the various system components of electronic device 500 such as the image processing unit 560, may include a metasurface for, for example, a POC device, according to the subject matter disclosed herein. The interface 540 may be configured to include a wireless interface that is configured to transmit data to or receive data from a wireless communication network using a RF signal. The wireless interface 540 may include, for example, an antenna, a wireless transceiver and so on. The electronic system 500 also may be used in a communication interface protocol of a communication system, such as, but not limited to, Code Division Multiple Access (CDMA), Global System for Mobile Communications (GSM), North American Digital Communications (NADC), Extended Time Division Multiple Access (E-TDMA), Wideband CDMA (WCDMA), CDMA2000, Wi-Fi, Municipal Wi-Fi (Muni Wi-Fi), Bluetooth, Digital Enhanced Cordless Telecommunications (DECT), Wireless Universal Serial Bus (Wireless USB), Fast low-latency access with seamless handoff Orthogonal Frequency Division Multiplexing (Flash-OFDM), IEEE 802.20, General Packet Radio Service (GPRS), iBurst, Wireless Broadband (WiBro), WiMAX, WiMAX-Advanced, Universal Mobile Telecommunication Service-Time Division Duplex (UMTS-TDD), High Speed Packet Access (HSPA), Evolution Data Optimized (EVDO), Long Term Evolution-Advanced (LTE-Advanced), Multichannel Multipoint Distribution Service (MMDS), and so forth.

Embodiments of the subject matter and the operations described in this specification may be implemented in digital electronic circuitry, or in computer software, firmware, or hardware, including the structures disclosed in this specification and their structural equivalents, or in combinations of one or more of them. Embodiments of the subject matter described in this specification may be implemented as one or more computer programs, i.e., one or more modules of computer-program instructions, encoded on computer-storage medium for execution by, or to control the operation of, data-processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer-storage medium can be, or be included in, a computer-readable storage device, a computer-readable storage substrate, a random or serial-access memory array or device, or a combination thereof. Moreover, while a computer-storage medium is not a propagated signal, a computer-storage medium may be a source or destination of computer-program instructions encoded in an artificially-generated propagated signal. The computer-storage medium can also be, or be included in, one or more separate physical components or media (e.g., multiple CDs, disks, or other storage devices). Additionally, the operations described in this specification may be implemented as operations performed by a data-processing apparatus on data stored on one or more computer-readable storage devices or received from other sources.

While this specification may contain many specific implementation details, the implementation details should not be construed as limitations on the scope of any claimed subject matter, but rather be construed as descriptions of features specific to particular embodiments. Certain features that are described in this specification in the context of separate embodiments may also be implemented in combination in a single embodiment. Conversely, various features that are described in the context of a single embodiment may also be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described herein. Other embodiments are within the scope of the following claims. In some cases, the actions set forth in the claims may be performed in a different order and still achieve desirable results. Additionally, the processes depicted in the accompanying figures do not necessarily require the particular order shown, or sequential order, to achieve desirable results. In certain implementations, multitasking and parallel processing may be advantageous.

As will be recognized by those skilled in the art, the innovative concepts described herein may be modified and varied over a wide range of applications. Accordingly, the scope of claimed subject matter should not be limited to any of the specific exemplary teachings discussed above, but is instead defined by the following claims.

What is claimed is:

1. A metasurface device, comprising:
a substrate;
a dielectric layer on the substrate, the dielectric layer comprising a top dielectric surface and a bottom dielectric surface that interfaces with a top surface of the substrate, the dielectric layer comprising a dielectric cylindrical cavity that extends between the top dielectric surface and the bottom dielectric surface;

an aluminum nanodisk in the dielectric cylindrical cavity, the aluminum nanodisk comprising a top nanodisk surface and a bottom nanodisk surface that interfaces with the top surface of the substrate; and an aluminum layer on the dielectric layer, the aluminum layer comprising a top aluminum surface and a bottom aluminum surface that interfaces with the top dielectric surface, the aluminum layer comprising an aluminum cylindrical cavity that extends between the top aluminum surface and the bottom aluminum surface, the aluminum cylindrical cavity corresponding to the dielectric cylindrical cavity, wherein a thickness of the aluminum nanodisk is selected to provide a span of the dielectric layer comprising polymethyl methacrylate (PMMA) between the bottom aluminum surface and the top nanodisk surface that is equal to or less than 10 nm, the span of the dielectric layer comprising PMMA enabling hybrid multipolar lossless plasmonic modes to enhance local electromagnetic fields.

2. The metasurface device of claim 1, wherein the dielectric layer comprises polymethyl methacrylate (PMMA).

3. The metasurface device of claim 2, wherein two or more analytes emit fluorescence in response to light of a predetermined wavelength being incident on the metasurface device and the two or more analytes being present at the dielectric layer.

4. The metasurface device of claim 3, wherein the two or more analytes emit fluorescence in a resonant mode of the metasurface device that is higher than a dipolar mode of the metasurface device.

5. The metasurface device of claim 3, wherein the two or more analytes comprises biomarkers for insulin, vascular endothelial growth factor (VEGF), and thrombin.

6. The metasurface device of claim 5, wherein a concentration of each of the two or more analytes is equal to 1 fmol in a single 10 µL droplet.

7. The metasurface device of claim 1, wherein a diameter of the at least one cylindrical cavity in the dielectric layer is equal to or less than 0.5 microns.

8. The metasurface device of claim 1, wherein the metasurface device comprises part of a point-of-care component of a smartphone.

* * * * *